United States Patent [19]
Wiklund et al.

[11] Patent Number: 5,411,027
[45] Date of Patent: May 2, 1995

[54] EQUIPMENT AND METHOD FOR TREATING CIRCULATORY ARREST

[76] Inventors: Lars Wiklund, Sveavägen 2, S-752 36 Uppsala; Bertil Hök, Flottiljgatan 55, S-721 31 Västeras, both of Sweden

[21] Appl. No.: 199,306
[22] PCT Filed: May 27, 1994
[86] PCT No.: PCT/SE93/00608
§ 371 Date: Mar. 8, 1994
§ 102(e) Date: Mar. 8, 1994
[87] PCT Pub. No.: WO94/01163
PCT Pub. Date: Jan. 20, 1994

[30] Foreign Application Priority Data
Jul. 3, 1992 [SE] Sweden .................. 9202062

[51] Int. Cl.⁶ .................. A61B 8/00; A61M 29/02
[52] U.S. Cl. .................. 128/660.03; 600/18; 607/122
[58] Field of Search .......... 128/653.1, 660.01, 660.03; 600/18; 623/3; 607/122

[56] References Cited
U.S. PATENT DOCUMENTS

| | | | |
|---|---|---|---|
| 3,556,079 | 1/1971 | Omizo | 128/662.05 |
| 4,459,977 | 7/1984 | Pizon et al. | 600/18 X |
| 4,489,730 | 12/1984 | Jingu | 128/662.05 |
| 4,552,127 | 11/1985 | Schiff | 600/18 |
| 4,771,765 | 9/1988 | Choy et al. | 600/18 |
| 4,793,351 | 12/1988 | Landman et al. | 604/99 X |
| 4,932,407 | 6/1990 | Williams | 607/122 X |
| 4,986,830 | 1/1991 | Owens et al. | 606/194 |
| 4,994,033 | 2/1991 | Shockey et al. | 604/101 |
| 5,058,593 | 10/1991 | Forestieri et al. | 128/661.07 |
| 5,195,942 | 3/1993 | Weil et al. | 600/18 |
| 5,242,374 | 9/1993 | Isoyama et al. | 600/18 |
| 5,253,647 | 10/1993 | Takahashi et al. | 128/653.1 |
| 5,308,319 | 5/1994 | Ide et al. | 600/18 |

*Primary Examiner*—Harris Jaworski
*Attorney, Agent, or Firm*—Watson, Cole, Grindle & Watson

[57] ABSTRACT

Apparatus for treatment of circulatory arrest includes a manually operated ultrasound probe (1) for localizing and puncture of a superficial artery (2) with a cannula (8) by which, subsequently, a catheter (10) is inserted towards the heart. The catheter (10) contains an elastically inflatable balloon (14,15) by which the distal aorta can be occluded, thereby making possible the injection of concentrated fluid through openings in the distal part of the catheter (10) from an ampoule (19) containing agents for activation of the cardiac muscle, for blood vessel dilation, for dissolving of blood clots or for protection against hypoxic injuries. The apparatus is controlled by a program stored in a memory unit (41) of a central processing unit (40). One or more pressure sensors (23), driving units (22), and pressure generators (21) are used to control the sequential processes.

10 Claims, 3 Drawing Sheets

EQUIPMENT AND METHOD FOR TREATING CIRCULATORY ARREST

BACKGROUND OF THE INVENTION

Adequate blood circulation is of vital importance to man and to all warm blooded animals. Death or loss of vital body functions occurs several minutes after acute circulatory arrest. There can be a number of causes for this, the most common of which are ventricular fibrillation and asystole, that is to say, conditions in which the heart muscle's periodic contractions stop. These conditions can be primary, that is, they can occur without any apparent reason. Other acute conditions such as blood clots in the pulmonary arteries or in the coronary arteries can secondarily produce the same circulatory effects.

All types of circulatory arrest are treatable in principle, but results are poor. A maximum of 50% of those who suffer such an arrest in the presence of a witness attain normal circulation again after treatment. The others die immediately, as a consequence of their disease, or too long a wait for effective treatment, or inadequate treatment. Of those patients who first regain spontaneous circulation, a large number later die. Circulatory arrest is consequently very difficult to treat, partly due to the short period of time available before damage occurs due to lack of oxygen. Today this treatment most often consists of a combination of different measures such as artificial respiration, compressions of the thorax, administration of cardiac stimulating medication, and short-duration electrical stimulation of the cardiac muscle, so-called defibrillation, by which ventricular fibrillation can often be stopped. By means of external cardiac compressions ("cardiac massage") some degree of blood circulation (5–10% of normal blood flow in vital organs) can be sustained, which along with artificial respiration provides a prolongation of the time period existing before irreversible damage occurs, from 3–4 minutes to a maximum of about 20 minutes. During this time it is in principle possible to go over to more effective forms of treatment. Use of the heart-lung machine, for example, is in the testing stage in certain places in the world. It has been demonstrated that the perfusion pressure of the blood and thereby the blood flow and the amount of oxygen delivered are in direct proportion to the chances of restoring normal circulation and other vital functions following a circulatory arrest. The present invention consists of an apparatus and method for more effective treatment of circulatory arrest, and the invention described here improves treatment of circulatory arrest in a substantially simpler, safer and less expensive but nevertheless much more effective way.

SUMMARY OF THE INVENTION

The invention makes it possible to attain central circulation by means of a retrograde balloon catheter within a very short period of time (one to two minutes), which initially results in a higher perfusion pressure in the vital organs and makes it possible to selectively inject pharmacological agents into the chambers of the heart, the coronary arteries, etc., and also makes it possible to defibrillate more effectively. The method consists of puncturing the skin over an artery, a suitable one being, for example, the femeral artery at the level of the groin, and using a special ultrasonic probe to localize this artery and insert a cannula. After exchanging the cannula for a larger access line by using the so-called Seldinger technique, a catheter is then inserted in the retrograde direction via the aorta up toward the heart. When the tip of the catheter has come up to the aortic arch, one or two catheter-encircling balloons are inflated, by means of which a tightening of the vessel walls is attained. The different subeffects which can be obtained using the specially adapted balloon catheter together constitue the total effect of treatment, which is radically better than that of previously existing techniques. A comparison between the simplicity of these measures, their cost, the absence of serious treatment risks and all the effects of treatment attained are surprisingly favorable for the present invention.

Use of this invention provides the following effects:

1. With simultaneous compressions of the thorax it increases arterial pressure in the part of the aorta nearest the heart (with the coronary arteries which start there), the carotid blood vessels (with the arteries to the brain which start there), and thereby also the blood flow and oxygen delivery to the heart and brain, and as an effect of this, the chances of reestablishing normal heart and pulmonary function in the patient are markedly increased.

2. It combines with these functions the chance to selectively administer very active medications to one or both of these vital organs. These medications can namely be given in a limited dose which, thanks to the fact that they are dispersed in the small blood volume contained in the proximal aorta and heart, can nevertheless attain therapeutic concentrations, and after passage through these organs the concentrations are decreased due to dilution in a larger part of the total blood volume, and the medications therefore do not risk causing undesirable or harmful effects in other parts of the body.

3. It consequently interrupts blood flow in the distal aorta during the initial phase of cardiopulmonary resusitation. This, however, does not constitute any difference when compared with the type of cardiopulmonary resusitation practiced all over the world (without mechanical occlusion of the aorta) where blood flow in the distal aorta is also approximately zero. Knowledge about this effect and also the effect obtained by minimizing the reduction which the distal aorta and abdominal contents cause in the pulse wave attained via compressions of the thorax, constitute the scientific basis for and application of the balloon catheter in this connection.

4. Furthermore, this invention makes it possible during rapid injection of fluid, possibly with the inclusion of medication, through the distal opening of the balloon catheter, which is pressing against the vessel wall, to obtain a temporary increase in pressure in the blood vessels located proximal to the balloon, or balloons, and thereby obtain an additional increase in blood flow in the heart and brain. This further increases the chances for the patient to regain normal heart and brain function.

5. The balloon catheter discussed above can also contain an electric conductor in one of its longitudinal lumens which terminates in the distal part of the balloon catheter with an electrode in direct contact with the blood and which can therefore be used as one of two electrodes for defibrillation, which then has a much greater effectiveness compared with electrodes placed on the skin. Concentration of the strength of the electrical field occurs in part via the smallness of the electrode and position directly next to the heart, and in part because a lower contact resistance to the electrode is obtained. In this way it is possible to obtain increased precision of treatment and a decrease in the necessary amount of energy needed for defibrillation. The latter results in an increased frequency of successful defibrillations and fewer pronounced secondary effects such as muscle contractions in and burns on pans of the body which otherwise are used as contact surfaces for the defibrillator's electrodes.

As a whole there are many significant advantages and no disadvantages other that those arising from technical difficulties involved in introducing the balloon catheter into the aorta with sufficient precision and speed. An important problem which can interfere with the application of the method is consequently the time factor. In principle, two possible solutions to this problem can be distinguished. One consists of having the practicing physician obtain via intensive training a very high degree of skill in the different techniques and, not least, attain a swiftness in making adequate decisions about different steps in the treatment. In practice, however, this has been shown to be difficult since acute and unexpected circulatory arrest are fortunately not so common in basic medical care.

With the present invention the problem of time is instead solved through several concurrent, constructive measures. The number of manual steps has been minimized in that the system is permanently assembled and ready for immediate use, aside from items which need to be sterilized and packaged separately. These are quickly attached to the system before use. In addition, time-consuming operations have been automated by sequence control in a computer according to a "program tree" where courses of events of different character are predicted and correct decisions after each step in the course of events are programmed in.

BRIEF DESCRIPTION OF THE DRAWINGS

The invention's characteristics are clear from the attached drawings, wherein.

DETAILED DESCRIPTION OF THE PREFERRED EMBODIMENT

Figure 1:
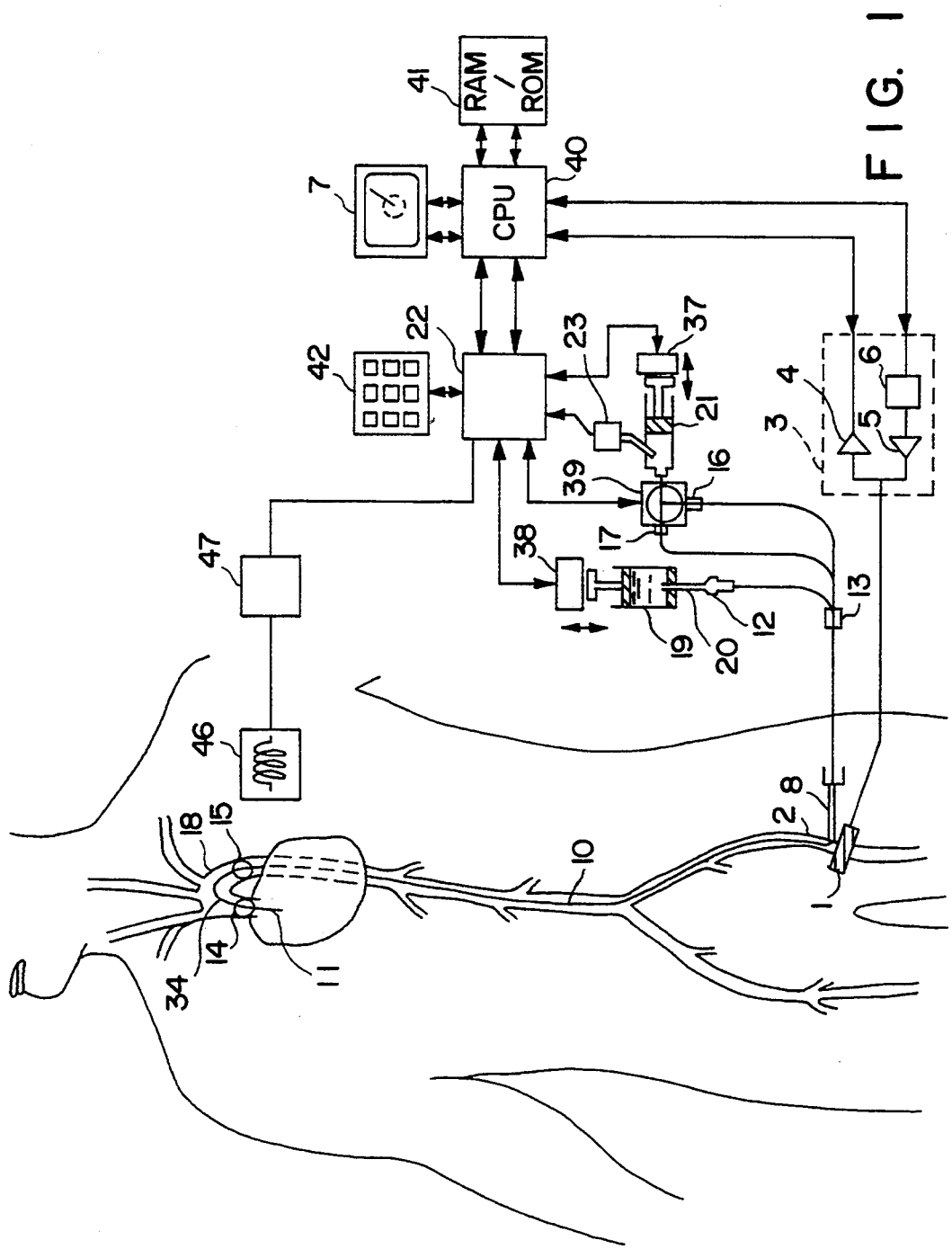
FIG. 1 shows a schematic overview of the construction of the apparatus.

FIG. 1 shows a schematic picture of the previously mentioned hand-maneuvered ultrasound probe 1 over a superficial artery such as the femoral artery. Alternative arteries are the carotid artery in the neck or the brachial artery in the bend of the arm. The ultrasound probe emits a pulsating ultrasound beam in the frequency area of 1–10 MHz and the shortest possible pulse length, typically several microseconds. When this ultrasound beam hits tissue layers with different acoustic impedance, reflection and spread occur that give rise to echoes which can be detected with the same ultrasound probe 1 that emits the ultrasound beam. Using known techniques, these echoes can be depicted on a screen 7. Furthermore, the ultrasound beam can be swept in a right angle to the direction of the artery and produce a cross section of the artery on the screen 7. Electrical operation of the ultrasound probe 1 is done from the electronic unit 3, which contains operating and amplifying circuits 5 for feeding in the ultrasound probe's emission of ultrasound beams, an amplifier 4 for detection of ultrasound echoes, and sweeping and modulating circuits 6 for synchronization of the sweep from the ultrasound beam with that on the screen 7. A tubular cannula 8 having a sharp tip which is inserted into the tissue in the ultrasound probe's picture domain will in this way be visible on the screen 7, and can be directed so that the artery 2 is punctured.

Using the Seldinger technique a catheter 10 can thereafter be inserted through the widened opening in the arterial wall and manually advanced up through the aorta and aortic arch 18 until it is right next to the heart. Injection of drugs can then occur through an opening in the catheter's distal end 11, the proximal end of which has a fluid (or gas) connection via a connector 12 with a receptacle 19 containing a solution or suspension of the drug to be administered. The choice of drug must be based on knowledge or suspicion of the cause of circulatory arrest. If a fine-wave ventricular fibrillation or asystole is seen on the ECG, then cardiac muscle stimulants can be used, while a clot-dissolving substance is chosen when infarct or embolus is suspected. The fluid receptacle 19 can, for example, be a puncturable ampule with which a 20-gauge needle can be used for rapid connection via the connector 12. Instillation can occur automatically, for instance by a piston movement directed by a motor 38, but can naturally also be done by hand using a corresponding piston movement.

The catheter 10 is equipped with an encircling balloon 14 situated near the tip of the catheter's opening 11. The balloon 14 can be inflated and made tight against the inner wall of the aorta 18. In this way fluid which is injected through the opening 11 in the tip of the catheter is prevented from spreading out into the general circulation. Instead, a concentrated effect is obtained in the heart chambers and central blood vessels. The balloon can be inflated because its interior has a pressure connection via a separate tube in the interior of the catheter 10, via a connector 16 and a valve 39, to a pressure generator 21. The apparatus can also be utilized to selectively inject drugs to the head, in particular to the brain. This can be done for example by using an additional balloon 15, which is placed 20–200 mm proximal to the previously described balloon 14. In a corresponding way, the balloon 15 is attached to the pressure generator 21 via the interior of catheter 10 by means of a branch 13 in the proximal part of the catheter to a connector 17 and valve 39, whose position determines which balloon, 13 or 14, should be connected to the pressure generator 21. If both balloons are tight against the aorta's 18 walls, the volume in between is delimited and accessible for selective injection of drugs. Connectors 12, 16 and 17 should be designed with stopcocks, or bayonet joints so that they cannot be confused and they should have a mechanical locking mechanism which prohibits inadvertent disconnection.

The balloon pressure is controlled by a pressure generator 21 which in the simplest design, with a gas as pressure medium, consists of an enclosed receptacle whose volume, and thereby pressure, is affected by a piston movement. The pressure is then conveyed via the catheter's 10 interior to balloon 14 and/or 15 which are closed via valve 39. The piston movement can be done by hand or by a motor 37. Inadvertent instillation of air in the circulatory system is injurious, since it can produce so-called air emboli, that is air bubbles which impede blood flow. The risk that this could happen if there were a leak can be eliminated either by using a liquid such as physiologic saline or a gas such as carbon dioxide, which is easily soluble in blood, and thereby prevent the occurrence of a two phase aggregation condition in the vascular system. The occurrence of leakage in the system is otherwise detected using a pressure sensor 23 connected to the pressure-set gas or fluid volume. Leakage is detected by characteristic decreases in pressure when the volume is held constant after pressure application.

The motors 37 and 38 and pressure sensor 23 are connected to the operating unit 22 which provides these with voltage and also brings back their control and measuring signals. A keyboard 42 is also connected, through which user-steered command signals can be fed in. All of the system's signals, in digital form, possibly after conversion from analog form where appropriate, pass through and are processed by the central processing unit 40, which is comprised of a general arithmetic/logical digital processing unit based on known techniques. This communicates in a known way through so-called lines to respective peripheral units. There is also a memory unit 41 which is of both a read/write type and a read type. The latter type is utilized as the memory for the program which provides the sequence of the course which is to result in stopping the circulatory arrest. The former type of memory is used for temporary storage of data such as arithmetical and logical functions.

It can be important for many reasons to be able to localize the catheter 10 and its different parts when it has been placed in the body. This can be done in a number of ways such as with the use of X-ray, which, however, is associated with special health risks due to the ionizing effect of the radiation. Another method is to equip the catheter 10 with one or more metallic pans such as an electrode 34 whose position can be determined with an inductive type of metal detector according to known technique. Such a conductor consists in part of an inductive coil 46 which carries high frequency alternating current from an electrical circuit 47, which also registers variations in the inductive load which a close metal object produces. The electronic circuit is further attached to the central processor via the operating unit 22.

Figure 2:
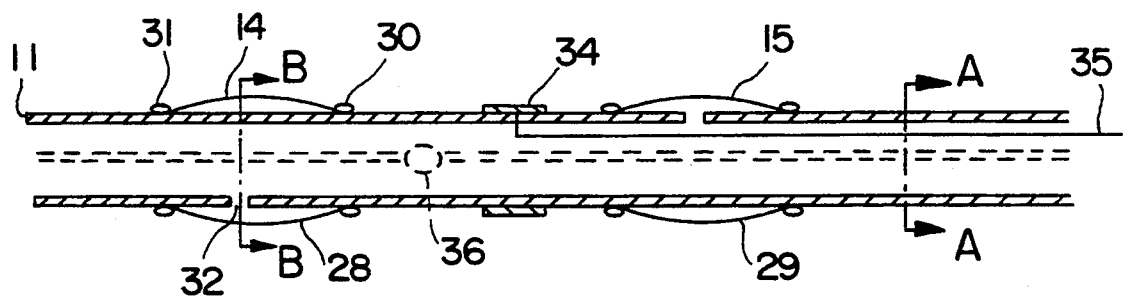
FIG. 2 shows the construction of the balloon catheter which is used to gain access to the central part of the circulatory system, and an example of the apparatus physical appearance is presented in FIG. 3.
Figure 2A:
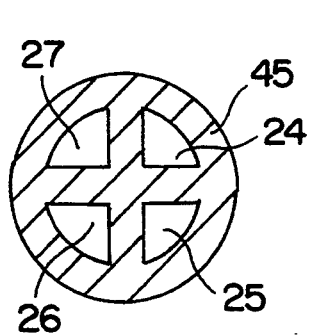
Figure 2B:
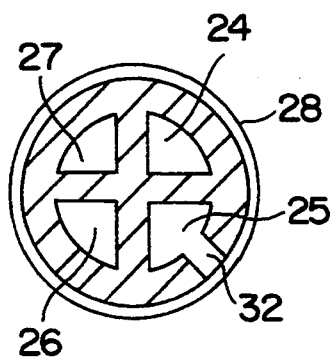

FIG. 2 shows the construction of the catheter 10 in more detail. There is a longitudinal section through its distal end and a cross section A—A through a section proximal to balloons 14 and 15, and a cross section B—B through the distal balloon 14. As is seen from cross section A—A, the catheter in this design is divided into four longitudinal chambers 24, 25, 26, 27. These are used to obtain a connection with the catheter tip 11, the balloons 14, 15, and a side hole 36 in the catheter's 10 wall between balloons 14 and 15 in order, as previously described, to make it possible to inject drugs in this section of the catheter. It is furthermore evident from the cross section that the balloon is held tight against the encasing surface of the catheter 10 by two sealing rings or adhesive rings 30, 31, which are squeezed into place. In addition, there are side holes 32, 33 in the catheter's 10 wall in order to allow for a connection between the respective cavities and the interior of the balloons 14 and 15. Finally, there is an electrode ring 34 of pure metal with a connection in the form of an isolated wire 35 along the entire length of the catheter. The electrode ring 34 is used in combination with another electrode such as one applied to the patient's skin, to provide voltage impulses with defibrillation. The catheter is appropriately made by pretension or of a polymer material such as polyethylene, polyurethane or fluoropolymer. Its outer and inner walls then constitute a continuous, homogeneous material. The balloons 14, 15 should be made as thin-walled tubes 28, 29, constructed of an elastomer such as latex or silicone.

Figure 3:
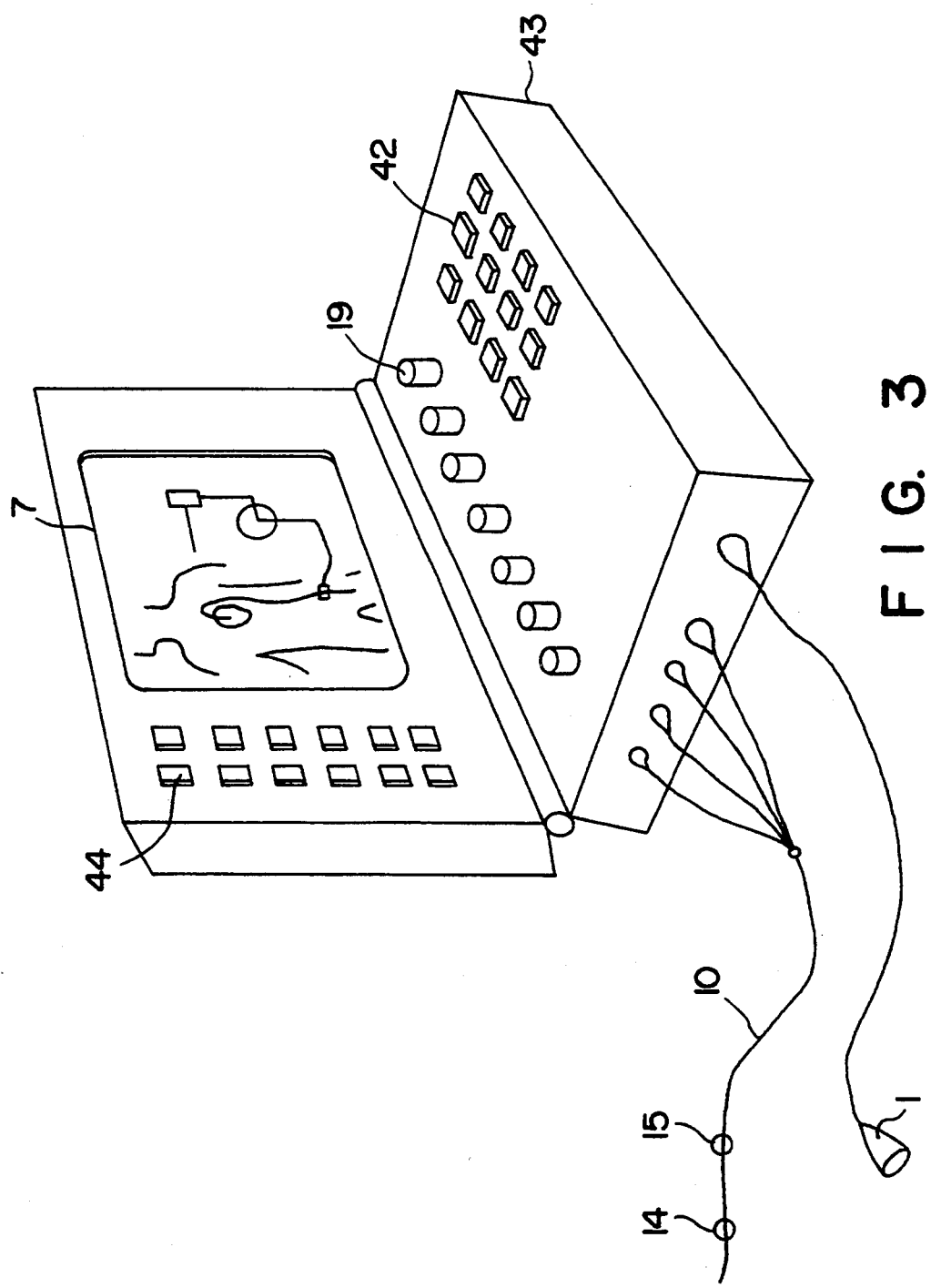

FIG. 3 shows the design of the apparatus. The entire system including a source of electrical energy, such as rechargeable batteries, is contained in a case 43. The catheter 10, with connections for fluid injection, and the balloons 14, 15 are connected via rapid connectors, as is the ultrasound probe 1. Receptacle 19 for different drugs is available for fast acquisition and connection. On the screen 7 information is given continuously to the user in alpha numeric or graphic form, both about the current condition of the apparatus and also as instructions for the next step in the process of terminating the circulatory arrest. The numerical indicator 44 provides additional information about the patient's vital parameters such as oxygen saturation, heart rate, respiratory rate, blood pressure, etc., via separate sensors. The method and apparatus comprising this invention can be varied in many ways within the framework for the following patent demands.

We claim:
1. An apparatus for treating circulatory arrest or other acute conditions affecting the heart and brain of a patient which comprises:
   a tubular cannula having a sharp tip which can be inserted into an artery of said patient, said cannula having a diameter smaller than a diameter of the artery into which it is inserted,
   a probe means for emitting ultrasound waves toward the skin of said patient and for receiving echoes of said ultrasound waves so as to locate the artery into which said tubular cannula is inserted,
   an electronic unit connected to said probe and containing drive and detection circuits and sweeping and modulation circuits for conversion of said echoes onto a display screen,
   catheter means including a tube having a proximal end and a distal end for passage through said tubular cannula into said artery and along said artery until said distal end thereof reaches a descending aorta of said patient, said catheter means including a first annular elastic balloon located between 20 and 250 mm from said distal end of said tube and inflatable to form a tight seal against an inner wall of said descending aorta, and defibrillation electrode means attached to said tube less than 200 mm from said distal end of said tube for internal defibrillation of a patient's heart, and
   electronic drive means for sending voltage pulses of adjustable energy to said defibrillation electrode means.

2. An apparatus according to claim 1, wherein said tube defines a first internal channel in communication with said first annular elastic balloon, and including a pressure generator in communication with said proximal end of said tube to supply fluid under pressure to said first internal channel to inflate said first annular elastic balloon.

3. An apparatus according to claim 2, wherein said tube defines a fluid discharge port at said distal end and a second internal channel therein in communication with said fluid discharge port, and including a receptacle means for liquid medicine in communication with said second internal channel, and an operating unit connected to control fluid supply to said first internal channel and liquid medicine supply to said second internal channel.

4. An apparatus according to claim 3, wherein said tube includes a second annular elastic balloon located between 20 and 200 mm away from said first annular elastic balloon in a direction toward said proximal end of said tube and wherein said tube defines a third internal channel in communication with said second annular elastic balloon to supply fluid under pressure thereto for inflation.

5. An apparatus according to claim 4, wherein said tube includes an opening therein to communicate one of said first, second and third internal channels to an environment around said tube.

6. An apparatus according to claim 3, including a central processing means for programmed steering and control of said electronic unit and said operating unit, said central processing means including a memory unit containing a program.

7. An apparatus according to claim 3, including a pressure sensor means connected between said pressure generator and said operating unit.

8. An apparatus according to claim 1, wherein said tube is composed of a polymer.

9. An apparatus according to claim 1, wherein said first annular elastic balloon is composed of a thin rubber membrane which surrounds said tube and two sealing rings which sealingly clamp opposite ends of said rubber membrane against said tube, and wherein said first internal channel communicates with said membrane between said sealing rings.

10. An apparatus according to claim 1, wherein said defibrillation electrode means comprises an annular metal ring surrounding said tube and wherein a metal wire extends from said metal ring into said tube and therewithin to said proximal end thereof.

* * * * *

UNITED STATES PATENT AND TRADEMARK OFFICE
CERTIFICATE OF CORRECTION

PATENT NO. : 5,411,027
DATED : May 2, 1995
INVENTOR(S) : Wiklund et al.

It is certified that error appears in the above-indentified patent and that said Letters Patent is hereby corrected as shown below:

In the title page item

[22] PCT Filed: July 2, 1993

Signed and Sealed this

Thirty-first Day of October 1995

Attest:

BRUCE LEHMAN

Attesting Officer        Commissioner of Patents and Trademarks